United States Patent [19]

Miki et al.

[11] Patent Number: 4,985,595
[45] Date of Patent: Jan. 15, 1991

[54] AMINOBENZAMIDE DERIVATIVES

[75] Inventors: Tosaku Miki; Masahide Asano; Toru Hosokami, all of Tokyo, Japan

[73] Assignee: Daiichi Pharmaceutical Co., Ltd., Tokyo, Japan

[21] Appl. No.: 279,256

[22] Filed: Dec. 1, 1988

Related U.S. Application Data

[63] Continuation of Ser. No. 65,815, Jun. 24, 1987, abandoned, which is a continuation of Ser. No. 804,723, Dec. 5, 1985, abandoned.

[30] Foreign Application Priority Data

Dec. 18, 1984 [JP] Japan .................................. 266828

[51] Int. Cl.$^5$ ............... C07C 237/44; C07C 271/28; C07C 309/24; A61K 31/165
[52] U.S. Cl. .................................. 564/157; 564/153; 560/27; 562/43; 562/44; 544/159; 544/165
[58] Field of Search ................... 564/157; 514/616

[56] References Cited

U.S. PATENT DOCUMENTS 4,297,357 10/1981 Miki et al. .................. 564/157 X

OTHER PUBLICATIONS

Barlow, Introduction to Chemical Pharmacology, 2nd Ed., John Wiley & Sons, Inc, N.Y., pp. 27, 32 & 33.
Takagi et al., Chem. Pharm. Bull., 12(4), 465–472.

*Primary Examiner*—Carolyn S. Elmore
*Attorney, Agent, or Firm*—Sughrue, Mion, Zinn, Macpeak & Seas

[57] ABSTRACT

Aminobenzamide derivatives of the formula (I)

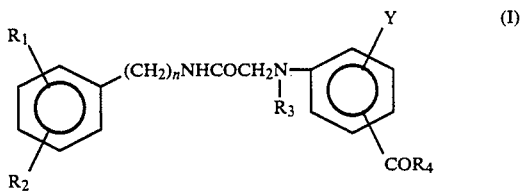

wherein:

$R_1$ and $R_2$ each represents a lower alkoxy group, $R_3$ represents a hydrogen atom, a lower alkyl group, a lower acyl group, a lower alkoxycarbonyl group or —$R_5$—$SO_3Z$, wherein $R_5$ represents a lower alkylene group and Z represents an alkali metal or an alkaline earth metal, $R_4$ represents an amino group, a morpholino group or a lower alkylamino group which may be substituted with a hydroxyl group at the alkyl moiety thereof, with the proviso that, when $R_3$ represents a hydrogen atom, $R_4$ cannot be an amino group, Y represents a hydrogen atom, a halogen atom or a lower alkoxy group, n represents an integer of from 1 to 6, and salts thereof; are disclosed. These compounds have excellent anti-peptic ulcer activities, and chemical and physical stabilities.

1 Claim, No Drawings

AMINOBENZAMIDE DERIVATIVES

This is a continuation of application Ser. No. 065,815 filed June 24, 1987, now abandoned which is a continuation of application Ser. No. 06/804,723 filed Dec. 5, 1985, now abandoned.

FIELD OF THE INVENTION

This invention relates to novel aminobenzamide derivatives and their salts which are useful as anti-peptic ulcer agents.

BACKGROUND OF THE INVENTION

Hitherto, various compounds having anti-ulcer activities have been disclosed in a number of publications. Of these known compounds, 2-(3-carbamoylphenylamino)-N-(3,4-dimethoxyphenethyl)acetamide is disclosed as anti-peptic ulcer agent in Japanese Patent Application (OPI) No. 31027/80 (the term "OPI" as used herein refers to a "published unexamined Japanese Patent Application"). Also, it is disclosed in Japanese Patent Application (OPI) No. 18947/81 that the hydrate of the above compound (hydrated crystals containing three molecules of crystallized water) has stable chemical and physical properties.

However, the above compounds do not necessarily have the sufficient anti-peptic ulcer activities and pharmaceutical properties.

SUMMARY OF THE INVENTION

This invention relates to aminobenzamide derivatives, and more particularly, to the compounds of the formula (I)

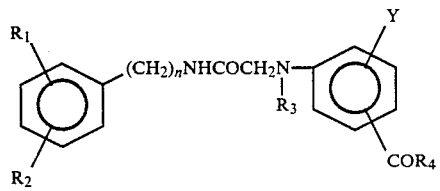

wherein:
$R_1$ and $R_2$ each represents a lower alkoxy group,
$R_3$ represents a hydrogen atom, a lower alkyl group, a lower acyl group, a lower alkoxycarbonyl group or $-R_5-SO_3Z$, wherein $R_5$ represents a lower alkylene group and Z represents an alkali metal or an alkaline earth metal,
$R_4$ represents an amino group, a morpholino group or a lower alkylamino group which may be substituted with a hydroxyl group at the alkyl moiety thereof, with the proviso that, when $R_3$ represents a hydrogen atom, $R_4$ cannot be an amino group,
Y represents a hydrogen atom, a halogen atom or a lower alkoxy group,
n represents an integer of from 1 to 6,
and salts thereof.

The compounds of this invention have excellent anti-peptic ulcer activities and chemical and physical stabilities for use as pharmaceutical preparations.

DETAILED DESCRIPTION OF THE INVENTION

This invention relates to aminobenzamide derivatives and salts thereof having the above formula (I).

In the above formula (I), the alkylamino group means a monoalkylamino group or a dialkylamino group wherein the alkyl groups may be the same or different.

The term "lower" as used herein for alkyl, alkoxy, acyl and alkylene groups means that such groups have 1 to 6 carbon atoms, preferably 1 to 3 cabon atoms.

The compounds of this invention can form an acid addition salt with an inorganic acid such as hydrochloric acid and sulfuric acid, or an organic acid such as picric acid.

In the above formula (I), $R_4$ is preferably a monoalkylamino group or an amino group, Y is preferably a hydrogen atom or an alkoxy group, n is preferably 2 and $R_3$ is preferably a hydrogen atom or $-R_5-SO_3Z$.

Particularly preferred compounds of this invention are as follows:
(1) 3-((2-(3,4-dimethoxyphenyl)ethyl)amino)-2-oxoethyl)amino)-N-methylbenzamide
(2) 3-((2-((2-(3,4-dimethoxyphenyl)ethyl)amino)-2-oxoethyl)amino)-N-ethylbenzamide
(3) 2-((2-((2-(3,4-dimethoxyphenyl)ethyl)amino)-2-oxoethyl)amino)-4-methoxy-N-methylbenzamide
(4) sodium N-(3-carbamoylphenyl)-N-(2-((2-(3,4-dimethoxyphenyl)ethyl)amino)-2-oxoethyl)aminomethanesulfonate.

Depending upon the type of substituents of $R_3$ and $R_4$, the compounds of this invention can be represented by the following formulae (Ia) and (Ib);

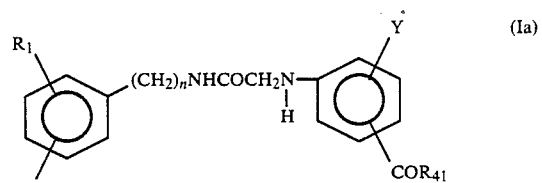

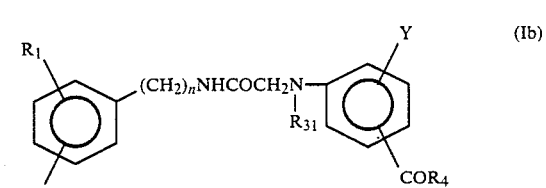

wherein:
$R_{31}$ represents a lower alkyl group, a lower acyl group, a lower alkoxycarbonyl group or $-R_5-SO_3-Z$,
$R_{41}$ represents a morpholino group or a lower alkylamino group which may be substituted with a hydroxyl group at the alkyl moiety thereof,
and $R_1$, $R_2$, $R_4$, Y, n, $R_5$ and Z represent the same as defined above.

The above compounds can be prepared by the processes as described below.

(a) Process for preparing the compounds of the formula (Ia)

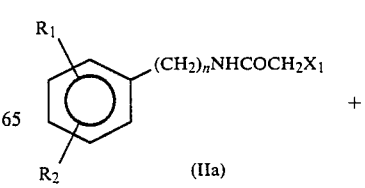

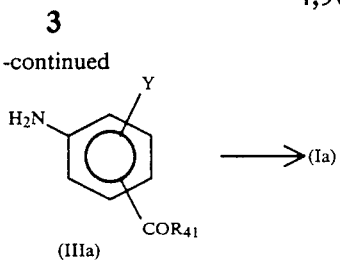

In the above reaction formula, $X_1$ represents a halogen atom, and $R_1$, $R_2$, Y, n and $R_{41}$ represent the same as defined above.

That is, the compound of the formula (Ia) can be prepared by reacting the compound of the formula (IIa) with the compound of the formula (IIIa) in the presence of an inert organic solvent or in the absence of a solvent. Also, the reaction can be carried out in the presence of an acid acceptor. The reaction can be carried out at a temperature of about 40° to about 80° C. for about 5 to about 24 hours. When the acid acceptor is used, the compound of formula (IIIa) and the acid acceptor each can be used at a molar ratio of 1 to 2 moles per mole of the compound of formula (IIa). When the acid acceptor is not used, the compound of formula (IIIa) can be employed in a molar excess amount, such as a molar ratio of 2 to 4 moles per mole of the compound of the formula (IIa). Examples of the acid acceptor include an alkali metal or an alkaline earth metal carbonate, hydroxide or oxide. Examples of the inert organic solvent include a halogenated hydrocarbon such as chloroform, an ether such as diethyl ether, an aromatic hydrocarbon such as benzene; pyridine, dimethylformamide and the like.

When an iodide such as sodium iodide is added to the reaction mixture, the reaction can be carried out more smoothly. The iodide is generally employed at a molar ratio of 1 to 2 moles per mole of the compound of the formula (IIIa). The amount of the solvent is usually in the range of 3 to 5 times (by weight) that of the compound of the formula (IIIa).

(b) Process for preparing the compound of the formula (Ib)

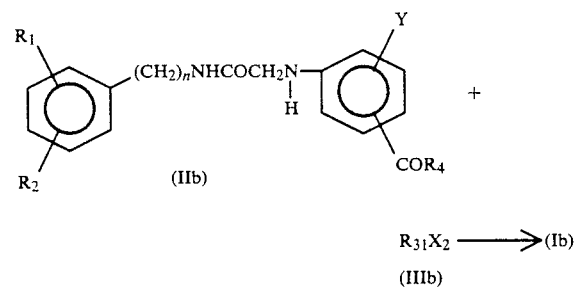

In the above reaction formula, $X_2$ represents a halogen atom, and $R_1$, $R_2$, $R_{31}$, $R_4$, Y and n represent the same as defined above.

That is, the compound of the formula (Ib) can be prepared by reacting the compound of the formula (IIb) with the compound of the formula (IIIb) in the presence of an inert solvent. Also, the reaction can be carried out in the presence of an acid acceptor. The reaction can be carried out at a temperature of from room temperature to about 80° C. for about 5 to about 24 hours. The compound of the formula (IIIb) can be employed at a molar ratio of 1 to 5 moles per mole of the compound of the formula (IIb). The acid acceptor can be employed at a ratio of 1 to 2 moles per mole of the compound of the formula (IIb). Examples of the acid acceptor include an alkali metal or alkaline earth metal carbonate, hydroxide or oxide. Examples of the solvent include a halogenated hydrocarbon such as chloroform; pyridine, dimethylformamide and the like. When a hydrated solvent of the above solvents is used, the reaction can be carried out more smoothly.

The compound of the formula (Ib), wherein $R_{31}$ represents a lower acyl group, can be prepared more smoothly by reacting the compound of the formula (IIb) with an anhydride of carboxylic acid corresponding to the lower acyl group in the presence of an acid acceptor such as an organic tertiary amine, for example pyridine, at a temperature of from room temperature to about 80° C. for about 5 to about 24 hours.

Also, the compound of the formula (Ib), wherein $R_{31}$ represents $-R_5-SO_3Z$, can be prepared more smoothly by reacting the compound of the formula (IIb) with a salt of hydroxyalkanesulfonic acid with an alkali metal or an alkaline earth metal in a suitable solvent such as water at a temperature of about 100° C. under refluxing for about 5 to about 24 hours. In this case, the salt of hydroxyalkanesulfonic acid can be employed at an mole equivalent amount or a slightly mole excess amount.

The thus-obtained compound of the formula (I) can be purified by conventional purification methods such as recrystallization, column chromatography and a combination thereof.

The starting materials of the formula (IIa) can be prepared according to the known method (Journal of Chemical Society, 1931, 36–49).

The starting materials of the formula (IIIa) can be prepared according to the known method (Biochemical Journal, vol 185, 775, (1980)) for preparing 3-amino-N-methylbenzamide which corresponds to the compound of the formula (IIIa) wherein Y represents a hydrogen atom and $-COR_4$ represents 3-$CONHCH_3$.

Also, the starting materials of the formula (IIb) can be prepared according to the method described in Japanese Patent Application (OPI) No. 31027/80 and the above process (a).

The anti-peptic ulcer activity of the compounds of this invention was confirmed by the following test, and the result obtained are shown in Table 1.

INHIBITORY EFFECT ON STRESS ULCER IN RAT

The inhibitory effects of the compounds of this invention on stress ulcer were confirmed according to restraint and water-immersion stress method disclosed in Japanese Journal of Pharmacology, vol 18, 9, (1968).

The compounds of this invention were administered orally to 7 rats weighing about 300 g in each group. After 30 minutes, they were immobilized and immersed in water at 21° C. for 7 hours to prepare the stress ulcer. Then, the inhibitory effects of the compounds of this invention on stress ulcer were confirmed.

TABLE 1

| Test Compound | Inhibitory Effect (%) | | |
|---|---|---|---|
| | 50 mg/kg | 100 mg/kg | 200 mg/kg |
| Compound a | 46** | 60** | 72** |
| Compound b | 30* | 53** | 63** |
| Compound c | 33* | 36* | 69** |
| Compound d | 34* | 36* | 42** |
| Compound e | 39** | 55** | 64** |

TABLE 1-continued

| Test Compound | Inhibitory Effect (%) | | |
|---|---|---|---|
| | 50 mg/kg | 100 mg/kg | 200 mg/kg |
| Compound f | 10 | 53** | 86** |
| Compound g | 45** | 41** | 65** |
| Control | | 23 | 36 |

*P < 0.05
**P < 0.01
Compound a: 3-((2-((2-(3,4-Dimethoxyphenyl)ethyl)amino)-2-oxoethyl)amino)-N-methylbenzamide
Compound b: 3-((2-((2-(3,4-Dimethoxyphenyl)ethyl)amino)-2-oxoethyl)amino)-N-ethylbenzamide
Compound c: 2-((2-((2-(3,4-Dimethoxyphenyl)ethyl)amino)-2-oxoethyl)amino)-4-methoxy-N-methylbenzamide
Compound d: Sodium N-(3-Carbomoylphenyl)-N-(2-((2-(3,4-dimethoxyphenyl)ethyl)amino)-2-oxoethyl)-aminomethanesulfonate
Compound e: 3-((2-((2-(3,4-Dimethoxyphenyl)ethyl)amino)-2-oxoethyl)amino)-N,N-dimethylbenzamide
Compound f: N-(2-(3,4-Dimethoxyphenyl)ethyl)-2-((3-morpholinocarbonylphenyl)amino)acetamide
Compound g: 2-((2-((2-(3,4-Dimethoxyphenyl)ethyl)amino)-2-oxoethyl)amino)-5-methoxy-N-methylbenzamide
Control: 2-(3-Carbamoylphenylamino)-N-(3,4-dimethoxy-phenethyl)acetamide Trihydrate As can be seen from the Table 1, the compounds of this invention exhibited very strong inhibitory effects on stress ulcer as compared with that of the control compound.

The compounds of this invention exhibited excellent inhibitory effects on several gastric ulcer models such as selotonine ulcer, alcohol ulcer, indomethacin ulcer and aspirin ulcer other than the stress ulcer. Also, the compounds of this invention exhibited an inhibitory effect on duodenal ulcer model such as cysteamine ulcer and dulcerozine ulcer.

Moreover, the compounds of this invention are chemically and physically stable, and such properties are particularly preferred in formulating the compounds as pharmaceutical preparations such as tablets, powders, capsules and granules.

The compounds of this invention exhibited low toxicity. For example, the acute toxicity (LD$_{50}$) of the Compound a, Compound c and Compound d was found to be more than 2 g/kg body weight in mice when orally administered.

The compounds of this invention can be administered orally or parenterally. These compounds can be administered at a dosage level of 30 to 600 mg in adult human per day in the form of tablets, capsules, powders, granules, injections, suppositories and the like.

The pharmaceutical preparations containing the compounds of this invention can be prepared by conventional techniques with appropriate additives such as lactose, corn starch, crystalline cellulose, calcium phosphate, hydroxypropyl cellulose, hydroxypropylmethyl cellulose, polyvinyl alcohol, carboxymethyl cellulose calcium, magnesium stearate and talc.

The present invention is further illustrated by the following Reference Examples and Examples, but the present invention is not limited thereto.

REFERENCE EXAMPLE 1

99.9 g of thionyl chloride was added to 35.0 g of 3-nitrobenzoic acid, and the mixture was refluxed for 2 hours. The excess thionyl chloride was distilled off, and dried benzene was added to the residue. The solvent was distilled off, and the residue was dissolved in 60 ml of chloroform. The solution was added dropwise to a mixture of 150 ml of 70% ethylamine aqueous solution and 1000 ml of chloroform with stirring in an ice-bath. The mixture was stirred for 30 minutes and 100 ml of water was added to the mixture. The chloroform solution was separated and washed successively with 10% hydrochloric acid, a 3% sodium bicarbonate aqueous solution and water. The chloroform solution was dried over sodium sulfate and concentrated in vacuo to give yellow crystals. The crystals were recrystallized from ethanol to give 34.7 g of N-ethyl-3-nitrobenzamide as yellow columnar crystals with m.p. 118° to 119.5° C.

17.0 g of the above product was dissolved in 600 ml of methanol, and 17 ml of Raney nickel was added to the solution. The mixture was catalytically reduced. After reduction, the catalyst was removed by filtration. The filtrate was concentrated in vacuo to give 13.4 g of 3-amino-N-ethylbenzamide as a colorless oil.

NMR (DMSO-d$_6$): δ: 1.09 (3H, t, 8 Hz), 3.07–3.46 (2H, m), 5.12 (2H, br), 6.56–7.16 (4H, m), 8.11 (1H, br).

According to the method described in Reference Example 1, the following compounds of the formulae (IV) and (V) were prepared.

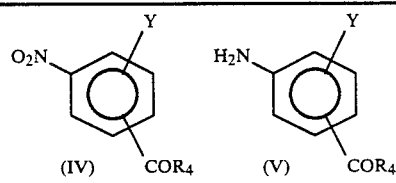

| Reference Example No. | Y | —COR$_4$ | Compound of formula (IV) m.p.(°C.) | Compound of formula (V) m.p.(°C.) |
|---|---|---|---|---|
| 2 | H | 3-CON(CH$_3$)$_2$ | 77–79 | 85–88 |
| 3 | H | 3-CON⟨O⟩ (morpholino) | 88–89 | 50–53 |
| 4 | H | 3-CONHCH$_2$CH$_2$OH | 134–135 | 102–103.5 |
| 5 | H | 3-CONHCH(CH$_3$)$_2$ | 131–132 | 147–149 |
| 6 | 5-Cl | 2-CONHCH$_3$ | 172–174 | 96–97 |
| 7 | 5-OCH$_3$ | 2-CONHCH$_3$ | 164–166 | 136–137 |
| 8 | 5-OCH$_3$ | 2-CONHC$_2$H$_5$ | 118–119 | 120–121 |
| 9 | 4-OCH$_3$ | 2-CONHCH$_3$ | 156–159 | 118–119 |
| 10 | 5-OCH$_3$ | 2-CON(CH$_3$)$_2$ | 102–104 | |
| 11 | 5-OCH$_3$ | 2-CON⟨O⟩ (morpholino) | 119–121 | 146–147 |

EXAMPLE 1

250 ml of dimethylformamide was added to a mixture of 68.6 g of 2-chloro-N-(2-(3,4-dimethoxyphenyl)ethyl)acetamide, 40.0 g of 3-amino-N-methylbenzamide, 39.9 g of sodium iodide and 53.8 g of calcium carbonate, and the resulting mixture was stirred for 7 hours at 45° to 50° C. After cooling, an insoluble material was removed by filtration, and the filtrate was concentrated in vacuo. The residue was extracted with 600 ml of chloroform and the extract was washed with a 5% sodium sulfite aqueous solution and then a saturated aqueous solution of sodium chloride. The washings were extracted with chloroform, and the extract was added to the above washed chloroform solution. The combined chloroform solution was dried over sodium sulfate, and the solvent was distilled off. The residue was dissolved in 100 ml of methanol, and 50 ml of concentrated hydrochloric acid was added to the methanol solution. The mixture was concentrated in vacuo, and ethanol was added to the residue. The solvent was distilled off to remove the azeotropic water. The residue was dissolved in 100 ml of ethanol, and diethyl ether was added to the solution. The precipitate formed was collected by filtration, washed with a mixture of ethanol and diethyl ether (1:2 by volume) and dried.

The precipitate was suspended in 1 liter of dichloroethane, and a 10% sodium carbonate aqueous solution was added to the suspension to make the solution alkaline. The dichloroethane solution was separated and washed with a saturated aqueous solution of sodium chloride. The washings were extracted with 400 ml of dichloroethane, and the extract was added to the above dichloroethane solution. The mixture was dried over sodium sulfate and the solvent was distilled off. A mixture of methanol and diethyl ether was added to the residue, and the precipitate formed was collected by filtration. The precipitate was recrystallized from a mixture of methanol and diethyl ether to give 51.0 g of 3-((2-((2-(3,4-dimethoxyphenyl)ethyl)amino)-2-oxoethyl)amino)-N-methylbenzamide as colorless needles with m.p. 93° to 96.5° C.

Analysis for $C_{20}H_{25}N_3O_4$: Calcd: C 64.67, H 6.78, N 11.31. Found: C 64.59, H 6.83, N 11.30.

NMR (DMSO-$d_6$): δ: 2.60 (2H, t, 7 Hz), 2.72 (3H, d, 5 Hz), 3.27 (2H, q, 7 Hz), 3.63 (2H, d, 6 Hz), 3.69 (6H, s), 5.97 (1H, t, 6 Hz), 6.49–7.22 (7H, m), 7.76 (1H, br), 8.13 (1H, br).

IR $\nu_{max}^{KBr}$ cm$^{-1}$: 1650 (C=O), 3320, 3370 (—NH).

The above precipitate was recrystallized from 100 ml of absolute methanol to give a product as colorless prisms with m.p. 133° to 134.5° C.

IR $\nu_{max}^{KBr}$ cm$^{-1}$: 1635, 1665 (C=O), 3350 (—NH).

The NMR data and the elemental analysis data of the above product as prisms were same as those of the product recrystallized from a mixture of methanol and diethyl ether. However, the m.p. and IR data were different between the two products. Therefore, the chemical structures of two product were the same, even though the crystal forms of these products were different.

EXAMPLE 2

75 ml of dimethylformamide was added to a mixture of 15.0 g of 2-chloro-N-(2-(3,4-dimethoxyphenyl)ethyl)acetamide, 9.5 g of 3-amino-N-ethylbenzamide, 8.7 g of sodium iodide and 11.6 g of calcium carbonate, and the mixture was stirred for 4.5 hours at 55° to 60° C. After cooling, an insoluble material was removed by filtration and, the filtrate was concentrated in vacuo. The residue was extracted with 500 ml of chloroform, and the extract was washed successively with a 10% sodium sulfite aqueous solution and a saturated aqueous solution of sodium chloride. The washings were extracted with 500 ml of chloroform, and the extract was added to the chloroform solution. The combined chloroform solution was dried over sodium sulfate, and the solvent was distilled off. 120 ml of 10% hydrochloric acid was added to the residue, and the mixture was washed 6 times with 30 ml of dichloroethane. The aqueous solution was made alkaline by adding sodium carbonate to form an aggluten-like material. The material was extracted with 300 ml of dichloroethane, and the extract was washed with a saturated aqueous solution of sodium chloride. The washings were extracted with 200 ml of dichloroethane. The extract was added to the above dichloroethane solution, and the mixture was dried over sodium sulfate. The solvent was distilled off, and the residue was purified by column chromatography on 390 g of silica gel using a mixture of ethyl acetate and ethanol (10:1 by volume) for elution to obtain a fraction containing a product. The solvent of the fraction was distilled off and the residue was recrystallized from a mixture of methanol and diethyl ether to give 10.0 g of 3-((2-((2-(3,4-dimethoxyphenyl)ethyl)amino)-2-oxoethyl)amino)-N-ethylbenzamide as colorless needles with m.p. 99° to 101° C.

Analysis for $C_{21}H_{27}N_3O_4$: Calcd: C 65.43; H 7.06, N 10.90. Found: C 65.55, H 7.17, N 10.78.

NMR (DMSO-$d_6$): δ: 1.09 (3H, t, 7.5 Hz), 2.61 (2H, t, 7 Hz), 3.05–3.43 (4H, m), 3.63 (2H, s), 3.69 (6H, s), 6.48–7.20 (7H, m), 7.73 (1H, br), 8.13 (1H, br).

According to the method described in Example 1 or 2, the following compounds of the formula (Ia) were prepared.

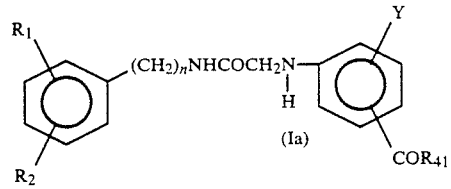

(Ia)

| Ex. No | $R_1$ | $R_2$ | Y | —$COR_{41}$ | n | m.p. (°C.) | NMR δ (DMSO-$d_6$) | Analysis Calcd Found C H N |
|---|---|---|---|---|---|---|---|---|
| 3 | 3-OCH$_3$ | 4-OCH$_3$ | H | 3-CON(CH$_3$)$_2$ | 2 | | 2.61(2H, t, 7Hz)<br>2.90(6H, s)<br>3.16–3.40(2H, m)<br>3.61(2H, d, 6Hz)<br>3.69(6H, s)<br>6.04(1H, t, 6Hz)<br>6.47–7.20(7H, m)<br>7.80(1H, br) | C 65.43 H 7.06 N 10.90<br>C 65.08 H 7.08 N 10.76 |

-continued

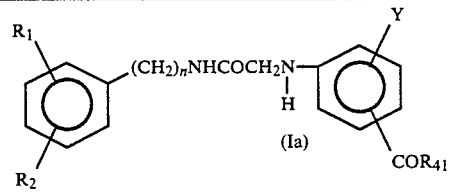
(Ia)

| Ex. No | R$_1$ | R$_2$ | Y | —COR$_{41}$ | n | m.p. (°C.) | NMR δ | Analysis Calcd Found C H N |
|---|---|---|---|---|---|---|---|---|
| 4 | 3-OCH$_3$ | 4-OCH$_3$ | H | 3-CON⌒O (morpholide) | 2 | | 2.62(2H, t, 7Hz)<br>3.08-3.75(12H, m)<br>3.69(6H, s)<br>6.38-7.23(7H, m)<br>7.80(1H, br) | C H N<br>64.62 6.84 9.83<br>64.66 7.02 9.74 |
| 5 | 3-OCH$_3$ | 4-OCH$_3$ | H | 3-CONH(CH$_2$)$_2$OH | 2 | | 2.61(2H, t, 7.5Hz)<br>3.15-3.73(8H, m)<br>3.70(6H, s)<br>6.50-7.23(7H, m)<br>7.75(1H, br)<br>8.10(1H, br) | C H N<br>62.82 6.78 10.47<br>63.18 6.87 10.48 |
| 6 | 3-OCH$_3$ | 4-OCH$_3$ | H | 3-CONHCH(CH$_3$)$_2$ | 2 | 109-111 | 1.16(6H, d, 6.5Hz)<br>2.62(2H, t, 6Hz)<br>3.30(2H, q, 6Hz)<br>3.68(8H, s)<br>6.50-7.23(7H, m)<br>7.68-8.08(2H, m)<br>(CDCl$_3$) | C H N<br>66.14 7.32 10.52<br>65.90 7.30 10.40 |
| 7 | 3-OCH$_3$ | 4-OCH$_3$ | H | 2-CONHCH$_3$ | 2 | 122.5-124 | 2.66(2H, t, 7Hz)<br>2.93(3H, d, 5Hz)<br>3.46(2H, q, 7Hz)<br>3.7-3.9(8H, m)<br>6.35-7.43(10H, m)<br>(DMSO-d$_6$) | C H N<br>64.67 6.78 11.31<br>64.56 6.79 11.17 |
| 8 | 3-OCH$_3$ | 4-OCH$_3$ | 5-Cl | 2-CONHCH$_3$ | 2 | 128-130 | 2.63(2H, t, 6Hz)<br>2.73(3H, d, 6Hz)<br>3.32(2H, br)<br>3.69(2H, s)<br>3.70(6H, s)<br>6.39-6.86(5H, m)<br>7.46(1H, d, 8Hz)<br>7.9(1H, br)<br>8.25(2H, br)<br>(CDCl$_3$) | C H N Cl<br>59.18 5.96 10.35 8.73<br>59.46 6.04 10.44 8.56 |
| 9 | 3-OCH$_3$ | 4-OCH$_3$ | 5-Cl | 2-CONHC$_2$H$_5$ | 2 | | 1.16(3H, t, 7Hz)<br>3.10-4.30(12H, m)<br>6.15-7.70(8H, m)<br>8.07(1H, br)<br>(DMSO-d$_6$) | C H N Cl<br>58.20 6.40 9.69 8.16<br>58.03 6.06 9.65 8.13<br>C$_{21}$H$_{26}$O$_4$N$_3$Cl.¾H$_2$O |
| 10 | 3-OCH$_3$ | 4-OCH$_3$ | 5-OCH$_3$ | 2-CONHCH$_3$ | 2 | 128-129 | 2.63(2H, t, 6Hz)<br>2.72(3H, d, 5Hz)<br>3.33(2H, br)<br>3.70(2H, s)<br>3.71(6H, s)<br>5.92(1H, d, 3Hz)<br>6.15(1H, dd, 9 and 3 Hz)<br>6.53-6.86(3H, m)<br>7.45(1H, d, 9Hz)<br>7.8-8.1(2H, m)<br>8.4(1H, m) | C H N<br>62.83 6.78 10.47<br>62.85 6.79 10.35 |
| 11 | 3-OCH$_3$ | 4-OCH$_3$ | 5-OCH$_3$ | 2-CONHC$_2$H$_5$ | 2 | | 1.09(3H, t, 7Hz)<br>2.62(2H, t, 6Hz)<br>3.00-4.00(15H, br)<br>5.82-6.80(5H, m)<br>7.45(1H, d, 8Hz)<br>7.55-8.50(3H, br) | C H N<br>62.25 7.12 9.90<br>62.35 7.04 9.32<br>C$_{22}$H$_{29}$N$_3$O$_5$.½H$_2$O |
| 12 | 3-OCH$_3$ | 4-OCH$_3$ | 4-OCH$_3$ | 2-CONHCH$_3$ | 2 | 114-116 | 2.62(2H, t, 6Hz)<br>2.74(3H, d, 5Hz)<br>3.30(2H, q, 6Hz)<br>3.63-3.76(11H, m)<br>6.20-7.10(6H, m)<br>7.50(1H, br)<br>7.80(1H, br)<br>6.20(1H, br)<br>(CDCl$_3$) | C H N<br>62.83 6.78 10.47<br>63.12 6.79 10.43 |
| 13 | 3-OCH$_3$ | 4-OCH$_3$ | 5-OCH$_3$ | 2-CON(CH$_3$)$_2$ | 2 | 106-107 | 2.69(2H, t, 7Hz)<br>3.04(6H, s) | C H N<br>63.60 7.04 10.11 |

-continued

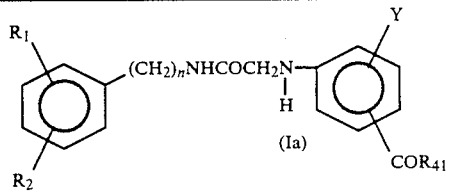

| Ex. No | R₁ | R₂ | Y | —COR₄₁ | n | m.p. (°C.) | NMR δ | Analysis Calcd Found | | |
|---|---|---|---|---|---|---|---|---|---|---|
| | | | | | | | 3.49(2H, q, 6Hz) 3.73(2H, s) 3.79(9H, s) 4.65(1H, br) 6.00–7.29(7H, m) | 63.78 | 7.20 | 10.10 |
| 14 | 3-OCH₃ | 4-OCH₃ | 5-OCH₃ | 2-CON⟨morpholino⟩ | 2 | 98–100 | 2.69(2H, t, 7Hz) 3.20–3.90(21H, m) 6.01–7.09(8H, m) | C 63.00 62.44 | H 6.83 7.00 | N 9.18 9.09 |
| 15 | 3-OCH₃ | 4-OCH₃ | H | 4-CONHCH₃ | 2 | 167–169 | 2.71(2H, t, 6Hz) 3.0(3H, br) 3.3–4.3(10H, m) 6.0–6.8(8H, m) 7.4–7.7(2H, m) | C 64.67 64.71 | H 6.78 6.79 | N 11.31 11.26 |

EXAMPLE 16

200 g of 2-(3-carbamoylphenylamino)-N-(3,4-dimethoxyphenethyl)acetamide trihydrate and 65.2 g of sodium hydroxymethanesulfonate were suspended in 400 ml of water, and the suspension was refluxed over night. After cooling, the reaction mixture was washed with chloroform, and an insoluble material was removed by filtration. The filtrate was concentrated in vacuo. The residue was dissolved in a mixture of 500 ml of water and 500 ml of ethanol under heating, and then the solution was cooled. The precipitate formed was collected by filtration and recrystallized from a mixture of water and ethanol to give 59.2 g of sodium N-(3-carbamoylphenyl)-N-(2-((2-(3,4-dimethoxyphenyl)ethyl)amino)-2-oxoethyl)aminomethanesulfonate dihydrate as colorless crystals with m.p. 253° to 255° C. (decomposition).

Analysis for $C_{20}H_{24}N_3O_7SNa \cdot 2H_2O$: Calcd: C 47.15, H 5.54, N 8.25. Found: C 47.11, H 5.39, N 8.34.

NMR (DMSO-$d_6$): δ: 2.57 (2H, t, 6 Hz), 3.4–3.1 (2H, br), 3.67 (6H, s), 4.05 (2H, br), 4.29 (2H, br), 6.47–7.33 (8H, m), 7.75 (1H, br), 8.26 (1H, br).

EXAMPLE 17

2-(3-Carbamoylphenylamino)-N-(3,4-dimethoxyphenethyl)acetamide (hereinafter referred to as Compound A) was reacted with calcium hydroxymethanesulfonate in the same manner as described in Example 16 to give calcium bis(N-(3-carbamoylphenyl)-N-(2-((2-(3,4-dimethoxyphenyl)ethyl)amino)-2-oxoethyl)aminomethanesulfonate hemihydrate as colorless crystals with m.p. 265° to 267° C. (decomposition).

Analysis for $C_{40}H_{48}N_6O_{14}S_2Ca \cdot \frac{1}{2}H_2O$: Calcd: C 50.57, H 5.20, N 8.85. Found: C 50.58, H 5.07, N 8.81.

NMR (DMSO-$d_6$): δ: 2.59 (4H, t, 7 Hz), 3.28 (4H, br), 3.70 (12H, s), 4.07 (4H, br), 4.30 (4H, br), 6.50–7.34 (16H, m), 7.73 (2H, br), 8.29 (2H, br).

EXAMPLE 18

3-((2-((2-(3,4-dimethoxyphenyl)ethyl)amino)-2-oxoethyl)amino)-N-methylbenzamide was reacted with sodium hydroxymethanesulfonate in the same manner as described in Example 16 to give sodium N-(2-((2-(3,4-dimethoxyphenyl)ethyl)amino)-2-oxoethyl)-N-(3-((methylamino)carbonyl)phenyl-aminomethanesulfonate with m.p. 187° to 190° C.

Analysis for $C_{21}H_{26}N_3O_7SNa$: Calcd: C 51.74, H 5.38, N 8.62. Found: C 51.46, H 5.34, N 8.65.

NMR (DMSO-$d_6$): δ: 2.58 (2H, m), 2.76 (3H, d, 4 Hz), 3.25 (2H, br), 3.68 (6H, s), 4.07 (2H, br), 4.30 (2H, br), 6.48–7.32 (7H, m), 8.12–8.40 (2H, br).

EXAMPLE 19

10.0 g of Compound A, 19.9 g of iodomethane and 31.0 g of potassium carbonate were added to 50 ml of dimethylformamide, and the mixture was stirred for 5 hours at 50° to 60° C. After cooling, the insoluble material was removed by filtration, and the filtrate was concentrated in vacuo. 100 ml of water and 500 ml of chloroform were added to the residue. The chloroform solution was separated and washed successively with a 10% sodium sulfite aqueous solution and 100 ml of water (3 times). The washings were extracted with chloroform, and the extract was added to the chloroform solution. The resulting solution was dried over sodium sulfate and concentrated in vacuo. The residue was crystallized from a mixture of ethanol and diethyl ether to give 3.2 g of yellow crystals. The crystals were recrystallized from ethanol to give 2.7 g of 3-(N-(2-(3,4-dimethoxyphenyl)ethyl)amino)-2-oxoethyl)-N-methylamino)benzamide as colorless crystals with m.p. 158.5° to 159.5° C.

Analysis for $C_{20}H_{25}N_3O_4$: Calcd: C 64.67, H 6.78, N 11.31. Found: C 64.26, H 6.75, N 11.15.

NMR (DMSO-$d_6$): δ: 2.61 (2H, t, 7.5 Hz), 2.95 (3H, s), 3.13–3.47 (2H, m), 3.69 (6H, s), 3.87 (2H, s), 6.50–7.30 (8H, m), 7.64–7.88 (2H, br).

EXAMPLE 20

A suspension of 5.1 g of Compound A, 60 ml of pyridine and 40 ml of acetic anhydride was stirred at room temperature overnight. The solvent was distilled off, and toluene was added to the residue. The toluene was distilled off. This procedure was carried out several times. The residue was crystallized from diethyl ether and the crystals obtained were recrystallized from chloroform to give 4.2 g of 3-(N-acetyl-N-(2-((2-(3,4-dimethoxyphenyl)ethyl)amino)-2-oxoethyl)amino)benzamide as colorless crystals with m.p. 111° to 113° C.

Analysis for $C_{21}H_{25}N_3O_5$: Calcd: C 63.14, H 6.31, N 10.52. Found: C 63.05, H 6.28, N 10.52.

NMR (DMSO-$d_6$): δ: 1.83 (3H, s), 2.6 (2H, t, 6 Hz), 3.1–3.5 (2H, m), 3.68 (6H, s), 4.16 (2H, s), 6.4–6.9 (3H, m), 7.25–8.05 (7H, m).

EXAMPLE 21

A mixture of 1.6 g of sodium hydroxide and 40 ml of water, and a mixture of 3.8 ml of ethyl chloroformate and 1 ml of chloroform were simultaneously added dropwise to a suspension of 7.0 g of Compound A and 200 ml of chloroform. The mixture was stirred at room temperature overnight. 0.3 g of sodium hydroxide and 0.6 ml of ethyl choroformate were added to the reaction mixture, and the mixture was allowed to react for 5 hours. 0.5 g of sodium hydroxide, 1 ml of ethyl chloroformate, a small amount of water and a small amount of chloroform were added to the reaction mixture, and the resulting mixture was stirred at room temperature overnight. The chloroform solution was separated and washed successively with diluted hydrochloric acid, an aqueous solution of sodium bicarbonate and an aqueous solution of sodium chloride. The washed chloroform solution was dried over sodium sulfate, and the solvent was distilled off. The residue was purified by silica gel column chromatography using a mixture of chloroform and methanol (197:1 by volume) for elution to give an amorphous product. The amorphous product was recrystallized from ethyl acetate to give 2.85 g of 3-(N-(2-((2-(3,4-dimethoxyphenyl)ethyl)amino)-2-oxoethyl)-N-(ethoxycarbonyl)amino)benzamide as colorless crystals with m.p. 104° to 105° C.

Analysis for $C_{22}H_{27}N_3O_6$: Calcd: C 61.53, H 6.34, N 9.78. Found: C 61.76, H 6.48, N 9.68.

NMR (DMSO-$d_6$): δ: 1.11 (3H, t, 7 Hz), 2.61 (2H, t, 7 Hz), 3.3 (2H, m), 3.68 (6H, s), 4.03 (2H, q, 7 Hz), 4.15 (2H, s), 6.5–6.9 (3H, m), 7.3 (1H, br), 7.2–7.8 (4H, m), 7.9 (2H, br).

EXAMPLE 22

2.0 g of 3-((2-((2-(3,4-dimethoxyphenyl)ethyl)amino)-2-oxoethyl)amino)-N-methylbenzamide (hereinafter referred to Compound B) was dissolved in 5 ml of ethanol, and 1 ml of concentrated hydrochloric acid was added to the solution. The mixture was concentrated in vacuo. Ethanol was added to the residue, and the solvent was distilled off to remove the azeotropic water. The residue was crystallized from a mixture of ethanol and diethyl ether. The crystals were collected by filtration and washed with a mixture of ethanol and diethyl ether (1:2 by volume). The crystals were dried to give 2.1 g of a hydrochloric acid addition salt of Compound B as colorless crystals with m.p. 118° to 130° C. (decomposition).

Analysis for $C_{20}H_{25}N_3O_4 \cdot HCl$: Calcd: C 58.89, H 6.43, N 10.30. Found: C 58.81, H 6.41, N 10.30.

According to the method as described in Example 22, salts represented by the following formula were prepared.

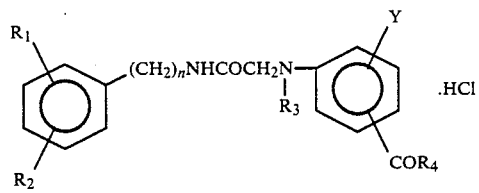

EXAMPLE 25

50 ml of water was added to 3.0 g of Compound B, and the mixture was shaken vigorously for 4.5 hours at room temperature. The mixture was allowed to stand overnight, and the precipitate formed was collected by filtration. The precipitate was air-dried for 4 days to give 2.8 g of the monohydrate of the Compound B as colorless prisms with m.p. 85° to 88° C.

Analysis for $C_{20}H_{25}N_3O_4 \cdot H_2O$: Calcd: C 61.68, H 6.99, N 10.79. Found: C 61.66, H 6.97, N 10.78.

IR $\nu_{max}^{KBr}$ cm$^{-1}$: 3550, 3350.

What is claimed is:

1. 3-((2-((2-(3,4-Dimethoxyphenyl)ethyl)amino)-2-oxoethyl)amino)-N-methylbenzamide or the pharmaceutically acceptable salt thereof.

* * * * *